US011058885B2

(12) United States Patent
Kim

(10) Patent No.: US 11,058,885 B2
(45) Date of Patent: Jul. 13, 2021

(54) WEARABLE CARDIOVERTER DEFIBRILLATOR (WCD) SYSTEM DETECTING VENTRICULAR TACHYCARDIA AND/OR VENTRICULAR FIBRILLATION USING VARIABLE HEART RATE DECISION THRESHOLD

(71) Applicant: West Affum Holdings Corp., Grand Cayman (KY)

(72) Inventor: Jaeho Kim, Redmond, WA (US)

(73) Assignee: West Affum Holdings Corp., Grand Cayman (KY)

( * ) Notice: Subject to any disclaimer, the term of this patent is extended or adjusted under 35 U.S.C. 154(b) by 78 days.

(21) Appl. No.: 16/197,638

(22) Filed: Nov. 21, 2018

(65) Prior Publication Data

US 2019/0160297 A1    May 30, 2019

Related U.S. Application Data

(60) Provisional application No. 62/592,070, filed on Nov. 29, 2017.

(51) Int. Cl.
*A61N 1/39* (2006.01)
*A61N 1/04* (2006.01)

(52) U.S. Cl.
CPC ......... *A61N 1/3987* (2013.01); *A61N 1/3904* (2017.08); *A61N 1/3925* (2013.01); *A61N 1/046* (2013.01); *A61N 1/0484* (2013.01)

(58) Field of Classification Search
CPC ..... A61N 1/3987; A61N 1/3904; A61N 1/046
See application file for complete search history.

(56) References Cited

U.S. PATENT DOCUMENTS 3,724,355 A    4/1973   Unger
3,724,455 A    4/1973   Unger
(Continued)

FOREIGN PATENT DOCUMENTS

WO    1998039061 A2    9/1998

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.
(Continued)

*Primary Examiner* — Allen Porter
*Assistant Examiner* — Andreanne A. Arnold
(74) *Attorney, Agent, or Firm* — Spectrum IP Law Group LLC

(57) ABSTRACT

A wearable cardioverter defibrillator (WCD) system according to embodiments is configured to be worn by an ambulatory patient, and to sense ECG signals of the patient. The WCD system includes a processor that extracts heart rate values from the ECG signals. If a heart rate value exceeds a decision threshold then, for subsequent heart rate values, the decision threshold may be lowered for administering a certain shock to the patient. In some embodiments the lowering is due to a cancel input being received, an intermediate shock having been administered, and so on. In some embodiments the decision threshold is lowered only temporarily. This may help with detecting a tachycardic event, and in particular with preventing the inhibiting of detecting such an event, as the patient's heart rate during such events may decrease while the heart's condition is deteriorating.

21 Claims, 9 Drawing Sheets

VARIABLE HEART RATE
DECISION THRESHOLD
(HYSTERESIS)

(56) References Cited

U.S. PATENT DOCUMENTS

| | | |
|---|---|---|
| 4,583,524 A | 4/1986 | Hutchins |
| 4,619,265 A | 10/1986 | Morgan et al. |
| 4,928,690 A | 5/1990 | Heilman et al. |
| 4,955,381 A | 9/1990 | Way et al. |
| 5,078,134 A | 1/1992 | Eilman et al. |
| 5,228,449 A | 7/1993 | Christ et al. |
| 5,348,008 A | 9/1994 | Bomn et al. |
| 5,353,793 A | 10/1994 | Bornn |
| RE34,800 E | 11/1994 | Hutchins |
| 5,394,892 A | 3/1995 | Kenny |
| 5,405,362 A | 4/1995 | Kramer et al. |
| 5,474,574 A | 12/1995 | Ayne et al. |
| 5,662,690 A | 9/1997 | Cole et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Moth et al. |
| 6,334,070 B1 | 12/2001 | Nova et al. |
| 6,356,785 B1 | 3/2002 | Snyder |
| 6,427,083 B1 | 7/2002 | Owen et al. |
| 6,437,083 B1 | 8/2002 | Brack et al. |
| 6,529,875 B1 | 3/2003 | Nakajima |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 10/2012 | Donnelly et al. |
| 8,369,944 B2 | 2/2013 | Macho et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,089,685 B2 | 7/2015 | Sullivan et al. |
| 9,131,901 B2 | 9/2015 | Volpe et al. |
| 9,132,267 B2 | 9/2015 | Kaib |
| 9,408,548 B2 | 8/2016 | Volpe et al. |
| 9,454,219 B2 | 9/2016 | Volpe et al. |
| 9,592,403 B2 | 3/2017 | Sullivan |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2008/0312709 A1 | 12/2008 | Volpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kalb et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0025131 A1 | 1/2014 | Sullivan et al. |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0328472 A1 | 11/2015 | Sullivan et al. |
| 2016/0004831 A1 | 1/2016 | Carlson et al. |
| 2016/0082277 A1 | 3/2016 | Foshee, Jr. et al. |
| 2016/0228718 A1* | 8/2016 | Koop ................ A61B 5/04525 |
| 2018/0020940 A1* | 1/2018 | Doerr ................ A61N 1/36514 607/4 |
| 2018/0168463 A1* | 6/2018 | Morris ................ A61B 5/686 |

OTHER PUBLICATIONS

Lifecor LifeVest System Model WCD 3100 Operator's Manual, 2006, PN 20B0040 Rev Fl, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

Pagan-Carlo, et al., "Encircling Overlapping Multipulse Shock Waveforms for Transthoracic Defibrillation," JACC Journals, Dec. 1998, vol. 32 Issue 7, p. 2065-2071.

* cited by examiner

SAMPLE COMPONENTS OF WEARABLE CARDIOVERTER DEFIBRILLATOR (WCD) SYSTEM

SAMPLE COMPONENTS OF EXTERNAL DEFIBRILLATOR

*VARIABLE HEART RATE DECISION THRESHOLD (HYSTERESIS)*

METHODS

METHODS

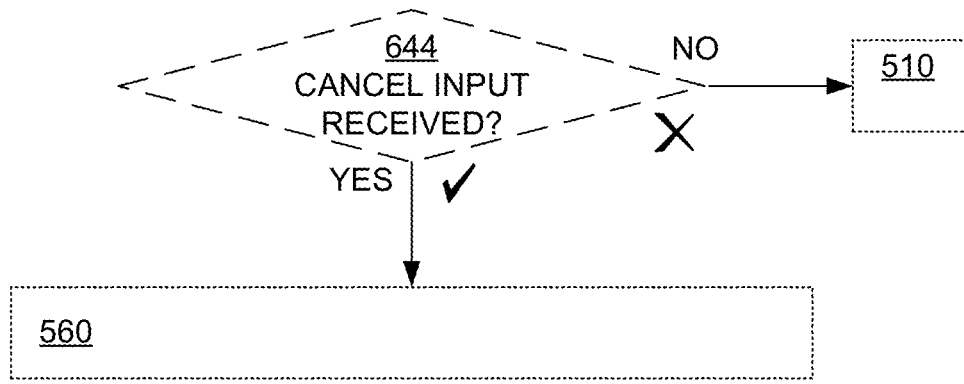
FIG. 6 — HEART RATE DECISION THRESHOLD WITH HYSTERESIS IF CANCEL INPUT RECEIVED
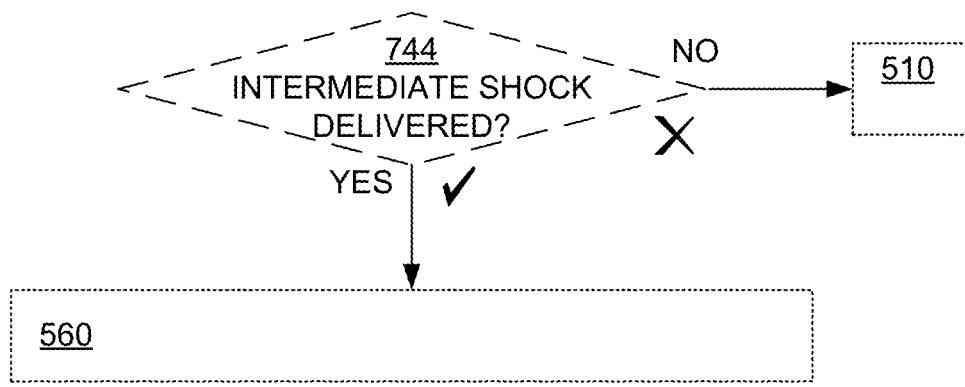
FIG. 7 — HEART RATE DECISION THRESHOLD WITH HYSTERESIS IF INTERMEDIATE SHOCK DELIVERED

METHODS

*METHODS*

WEARABLE CARDIOVERTER DEFIBRILLATOR (WCD) SYSTEM DETECTING VENTRICULAR TACHYCARDIA AND/OR VENTRICULAR FIBRILLATION USING VARIABLE HEART RATE DECISION THRESHOLD

CROSS REFERENCE TO RELATED PATENT APPLICATIONS

This patent application claims priority from U.S. Provisional Patent Application Ser. No. 62/592,070, filed on Nov. 29, 2017.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim. Some observers have thought that SCA is the same as a heart attack, which it is not.

Some people have an increased risk of SCA. Such people include patients who have had a heart attack, or a prior SCA episode. A frequent recommendation for these people is to receive an Implantable Cardioverter Defibrillator (ICD). The ICD is surgically implanted in the chest, and continuously monitors the patient's electrocardiogram (ECG). If certain types of heart arrhythmias are detected, then the ICD delivers an electric shock through the heart.

As a further precaution, people who have been identified to have an increased risk of an SCA are sometimes given a Wearable Cardioverter Defibrillator (WCD) system, to wear until the time that their ICD is implanted. Early versions of such systems were called wearable cardiac defibrillator systems. A WCD system typically includes a harness, vest, belt, or other garment that the patient is to wear. The WCD system further includes electronic components, such as a defibrillator and electrodes, coupled to the harness, vest, or other garment. When the patient wears the WCD system, the electrodes may make good electrical contact with the patient's skin, and therefore can help sense the patient's ECG. If a shockable heart arrhythmia is detected from the ECG, then the defibrillator delivers an appropriate electric shock through the patient's body, and thus through the heart. This may restart the patient's heart and thus save their life.

All subject matter discussed in this Background section of this document is not necessarily prior art, and may not be presumed to be prior art simply because it is presented in this Background section. Plus, any reference to any prior art in this description is not, and should not be taken as, an acknowledgement or any form of suggestion that such prior art forms parts of the common general knowledge in any art in any country. Along these lines, any recognition of problems in the prior art discussed in this Background section or associated with such subject matter should not be treated as prior art, unless expressly stated to be prior art. Rather, the discussion of any subject matter in this Background section should be treated as part of the approach taken towards the particular problem by the inventor. This approach in and of itself may also be inventive.

BRIEF SUMMARY

The present description gives instances of wearable cardioverter defibrillator (WCD) systems, storage media that may store programs, and methods, the use of which may help overcome problems and limitations of the prior art.

A wearable cardioverter defibrillator (WCD) system according to embodiments is configured to be worn by an ambulatory patient, and to sense ECG signals of the patient. The WCD system includes a processor that extracts heart rate values from the ECG signals. If a heart rate value exceeds a decision threshold then, for subsequent heart rate values, the decision threshold may be lowered for administering a certain shock to the patient. In some embodiments the lowering is due to a cancel input being received, an intermediate shock having been administered, and so on. In some embodiments the decision threshold is lowered only temporarily.

An advantage can be that this reduction of the decision threshold may help with detecting a tachycardic event, and in particular with preventing the inhibiting of detecting such an event, as the heart rate during such events may decrease while the heart's condition is deteriorating.

These and other features and advantages of the claimed invention will become more readily apparent in view of the embodiments described and illustrated in this specification, namely in this written specification and the associated drawings.

BRIEF DESCRIPTION OF THE DRAWINGS

FIG. 6 is a flowchart segment that can be used for an operation of the flowchart of FIG. 5, according to an embodiment.

FIG. 7 is a flowchart segment that can be used for an operation of the flowchart of FIG. 5, according to an embodiment.

DETAILED DESCRIPTION

As has been mentioned, the present description is about wearable cardioverter defibrillator (WCD) systems, storage media that may store programs, and methods. Embodiments are now described in more detail.

A wearable cardioverter defibrillator (WCD) system according to embodiments may protect an ambulatory patient by electrically restarting their heart if needed. Such a WCD system may have a number of components. These components can be provided separately as modules that can be interconnected, or can be combined with other components, and so on.

Figure 1:
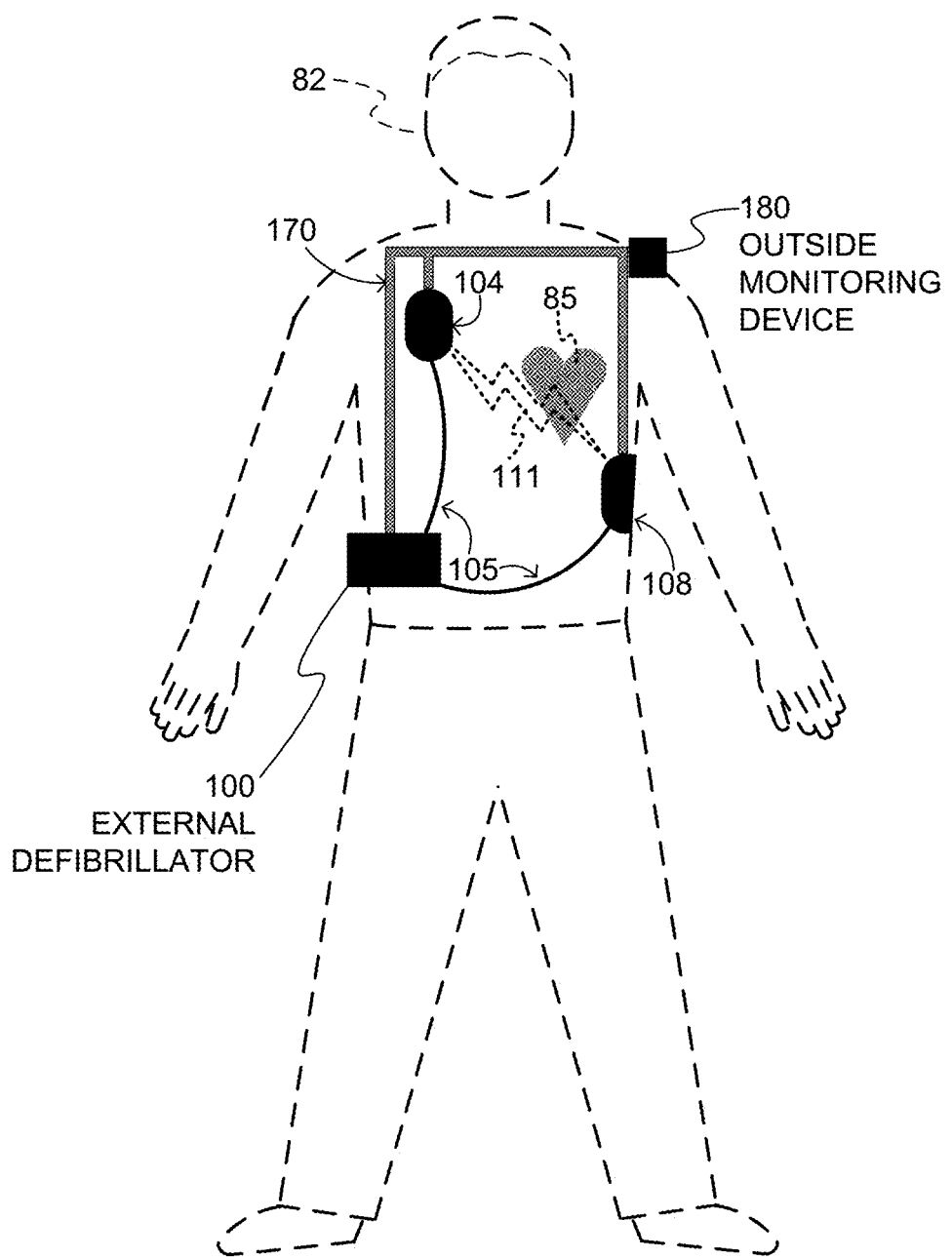
FIG. 1 is a diagram of components of a sample wearable cardioverter defibrillator (WCD) system, made according to embodiments.

FIG. 1 depicts a patient 82. Patient 82 may also be referred to as a person and/or wearer, since the patient is wearing components of the WCD system. Patient 82 is ambulatory, which means that, while wearing the wearable portion of the WCD system, patient 82 can walk around and is not necessarily bed-ridden. While patient 82 may be considered to be also a "user" of the WCD system, this is not a requirement. For instance, a user of the wearable cardioverter defibrillator (WCD) may also be a clinician such as a doctor, nurse, emergency medical technician (EMT) or other similarly tasked individual or group of individuals. In some cases, a user may even be a bystander. The particular context of these and other related terms within this description should be interpreted accordingly.

A WCD system according to embodiments can be configured to defibrillate the patient who is wearing the designated parts the WCD system. Defibrillating can be by the WCD system delivering an electrical charge to the patient's body in the form of an electric shock. The electric shock can be delivered in one or more pulses.

In particular, FIG. 1 also depicts components of a WCD system made according to embodiments. One such component is a support structure 170 that is wearable by ambulatory patient 82. Accordingly, support structure 170 is configured to be worn by ambulatory patient 82 for at least several hours per day, and for at least several days, even a few months. It will be understood that support structure 170 is shown only generically in FIG. 1, and in fact partly conceptually. FIG. 1 is provided merely to illustrate concepts about support structure 170, and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to analogous articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient's body by adhesive material, for example as shown and described in U.S. Pat. No. 8,024,037. Support structure 170 can even be implemented as described for the support structure of US Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/0056682 document. There can be other examples.

FIG. 1 shows a sample external defibrillator 100. As described in more detail later in this document, some aspects of external defibrillator 100 include a housing and an energy storage module within the housing. As such, in the context of a WCD system, defibrillator 100 is sometimes called a main electronics module. The energy storage module can be configured to store an electrical charge. Other components can cause at least some of the stored electrical charge to be discharged via electrodes through the patient, so as to deliver one or more defibrillation shocks through the patient.

FIG. 1 also shows sample defibrillation electrodes 104, 108, which are coupled to external defibrillator 100 via electrode leads 105. Defibrillation electrodes 104, 108 can be configured to be worn by patient 82 in a number of ways. For instance, defibrillator 100 and defibrillation electrodes 104, 108 can be coupled to support structure 170, directly or indirectly. In other words, support structure 170 can be configured to be worn by ambulatory patient 82 so as to maintain at least one of electrodes 104, 108 on the body of ambulatory patient 82, while patient 82 is moving around, etc. The electrode can be thus maintained on the body by being attached to the skin of patient 82, simply pressed against the skin directly or through garments, etc. In some embodiments the electrode is not necessarily pressed against the skin, but becomes biased that way upon sensing a condition that could merit intervention by the WCD system. In addition, many of the components of defibrillator 100 can be considered coupled to support structure 170 directly, or indirectly via at least one of defibrillation electrodes 104, 108.

When defibrillation electrodes 104, 108 make good electrical contact with the body of patient 82, defibrillator 100 can administer, via electrodes 104, 108, a brief, strong electric pulse 111 through the body. Pulse 111 is also known as shock, defibrillation shock, therapy, electrotherapy, therapy shock, etc. Pulse 111 is intended to go through and restart heart 85, in an effort to save the life of patient 82. Pulse 111 can further include one or more pacing pulses of lesser magnitude to simply pace heart 85 if needed, and so on.

External defibrillator 100 may decide whether or not to defibrillate based on specially processing an ECG signal of the patient. Moreover, external defibrillator 100 may initiate defibrillation, or hold-off defibrillation, based on a variety of inputs, with the ECG signal merely being one of these inputs.

A WCD system according to embodiments can obtain data from patient 82. For collecting such data, the WCD system may optionally include at least an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document.

For some of these parameters, device 180 may include one or more sensors or transducers. Each one of such sensors can be configured to sense a parameter of patient 82, and to render an input responsive to the sensed parameter. In some embodiments the input is quantitative, such as values of a sensed parameter; in other embodiments the input is qualitative, such as informing whether or not a threshold is crossed, and so on. Sometimes these inputs about patient 82 are also called physiological inputs and patient inputs. In embodiments, a sensor can be construed more broadly, as encompassing many individual sensors.

Optionally, device 180 is physically coupled to support structure 170. In addition, device 180 may be communicatively coupled with other components that are coupled to support structure 170. Such communication can be implemented by a communication module, as will be deemed applicable by a person skilled in the art in view of this description.

In embodiments, one or more of the components of the shown WCD system may be customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. The measured values of such baseline physiological parameters can be used to customize the WCD system, in order to make its diagnoses more accurate, since patients' bodies differ from one another. Of course, such parameter values can be stored in a memory of the WCD system, and so on. Moreover, a programming interface can be made according to embodiments, which receives such measured values of baseline physiological parameters. Such a programming interface may input automatically in the WCD system these, along with other data.

Figure 2:
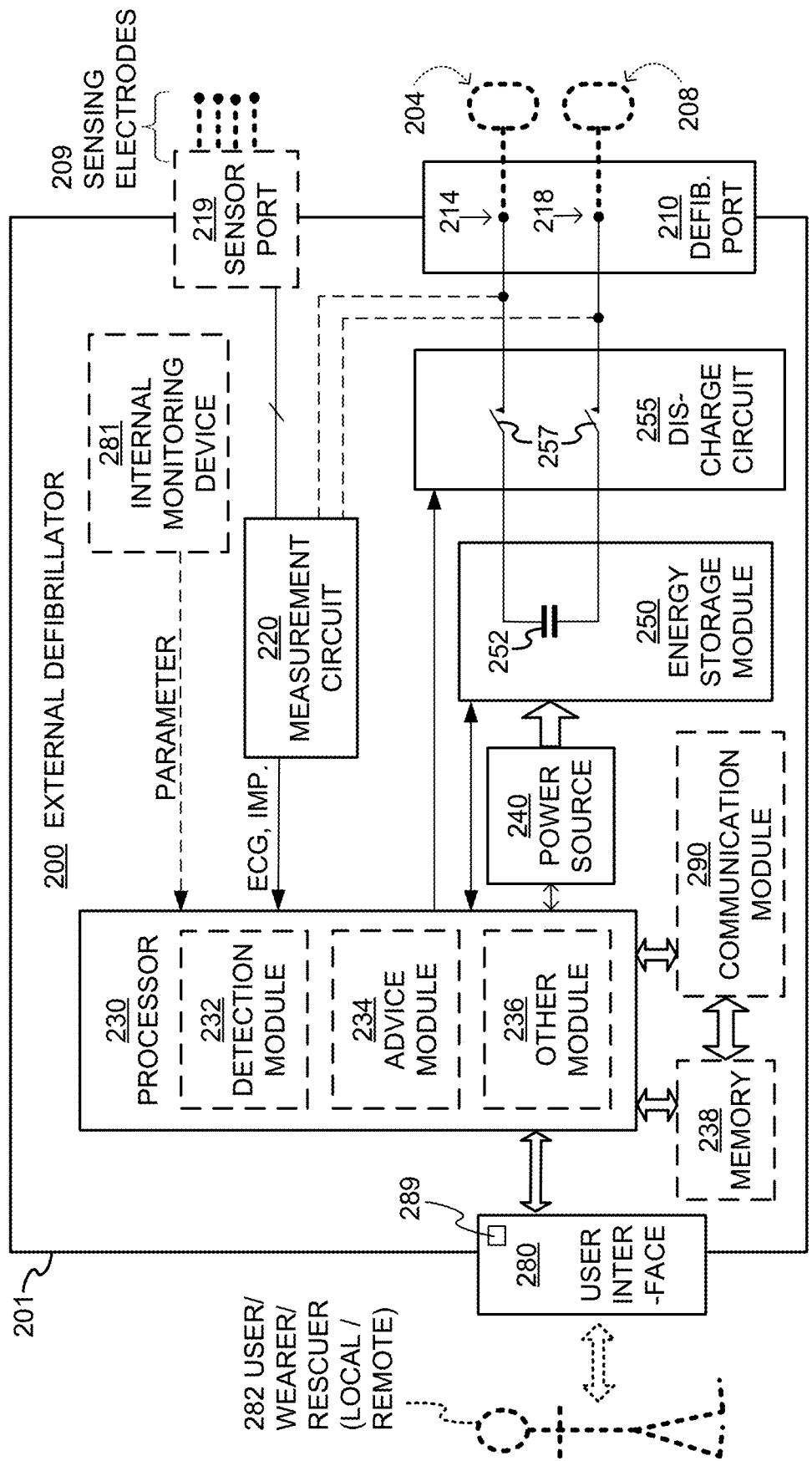
FIG. 2 is a diagram showing sample components of an external defibrillator, such as the one belonging in the system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as ambulatory patient 82 of FIG. 1. Defibrillator 200 may further include a user interface 280 for a user 282. User 282 can be patient 82, also known as wearer 82. Or, user 282 can be a local rescuer at the scene, such as a bystander who might offer assistance, or a trained person. Or, user 282 might be a remotely located trained caregiver in communication with the WCD system.

User interface 280 can be made in a number of ways. User interface 280 may include output devices, which can be visual, audible or tactile, for communicating to a user by outputting images, sounds or vibrations. Images, sounds, vibrations, and anything that can be perceived by user 282 can also be called human-perceptible indications (HPIs). There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds and/or words to warn bystanders, etc.

User interface 280 may further include input devices for receiving inputs from users. Such input devices may include various controls, such as pushbuttons, keyboards, touchscreens, one or more microphones, and so on. An input device can be a cancel switch 289, which is sometimes called an "I am alive" switch or "live man" switch. In some embodiments, actuating cancel switch 289 can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which of monitoring devices 180, 281 can be done according to design considerations. Device 281 may include one or more sensors, as also described elsewhere in this document.

Patient parameters may include patient physiological parameters. Patient physiological parameters may include, for example and without limitation, those physiological parameters that can be of any help in detecting by the WCD system whether or not the patient is in need of a shock or other intervention or assistance. Patient physiological parameters may also optionally include the patient's medical history, event history and so on. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include one or more electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an $SpO_2$ sensor, and so on. In view of this disclosure, it will be appreciated that such sensors can help detect the patient's pulse, and can therefore also be called pulse detection sensors, pulse sensors, and pulse rate sensors. In addition, a person skilled in the art may implement other ways of performing pulse detection.

Patient state parameters include recorded aspects of patient 282, such as motion by a motion detector, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

System parameters of a WCD system can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether or not it is likely raining. Presumed patient location could also be considered an environmental parameter. The patient location could be presumed, if monitoring device 180 or 281 includes a GPS location sensor as per the above, and if it is presumed that the patient is wearing the WCD system.

Defibrillator 200 typically includes a defibrillation port 210, which can be a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer at least some of the electrical charge that has been stored in an energy storage module 250 that is described more fully later in this document. The electric charge will be the shock for defibrillation, pacing, and so on.

Defibrillator 200 may optionally also have a sensor port 219 in housing 201, which is also sometimes known as an ECG port. Sensor port 219 can be adapted for plugging in sensing electrodes 209, which are also known as ECG electrodes and ECG leads. It is also possible that sensing electrodes 209 can be connected continuously to sensor port 219, instead. Sensing electrodes 209 are types of transducers that can help sense an ECG signal, e.g. a 12-lead signal, or a signal from a different number of leads, especially if they make good electrical contact with the body of the patient and in particular with the skin of the patient. As with defibrillation electrodes 204, 208, the support structure can be configured to be worn by patient 282 so as to maintain sensing electrodes 209 on a body of patient 282. For example, sensing electrodes 209 can be attached to the inside of support structure 170 for making good electrical contact with the patient, similarly with defibrillation electrodes 204, 208.

For purposes of this document, a first electrode could be a defibrillation electrode, such as one of defibrillation electrodes 204, 208. In addition, a second electrode that may be configured to sense an electrocardiogram (ECG) signal of ambulatory patient 282 could be either one of sensing electrodes 209, or one of defibrillation electrodes 204, 208.

In some embodiments, defibrillator 200 also includes a measurement circuit 220, as one or more of its sensors or transducers. Measurement circuit 220 senses one or more electrical physiological signals of the patient from sensor port 219, if provided. Even if defibrillator 200 lacks sensor port 219, measurement circuit 220 may optionally obtain physiological signals through nodes 214, 218 instead, when defibrillation electrodes 204, 208 are attached to the patient. In these cases, the input reflects an ECG measurement. The patient parameter can be an ECG signal, which can be sensed as a voltage difference between electrodes 204, 208. In addition, the patient parameter can be an impedance, which can be sensed between electrodes 204, 208 and/or between the connections of sensor port 219 considered pairwise. Sensing the impedance can be useful for detecting, among other things, whether these electrodes 204, 208 and/or sensing electrodes 209 are not making good electrical contact with the patient's body. These patient physiological signals may be sensed when available. Measurement circuit 220 can then render or generate information about them as inputs, data, other signals, etc. More strictly speaking, the information rendered by measurement circuit 220 is output from it, but this information can be called an input because it is received as an input by a subsequent device or functionality.

Defibrillator 200 also includes a processor 230. Processor 230 may be implemented in a number of ways. Such ways include, by way of example and not of limitation, digital and/or analog processors such as microprocessors and Digital Signal Processors (DSPs) controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as inputs, data that reflect values, or other signals, may be used by the VF detector to determine whether the patient is experiencing VF. Detecting VF is useful, because VF typically results in SCA. Detection module 232 can also include a Ventricular Tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments, and determine whether or not a shock criterion is met. The determination can be made from a rhythm analysis of the captured ECG signal or otherwise.

In some embodiments, when the determination is to shock, an electrical charge is delivered to the patient. Delivering the electrical charge is also known as discharging and shocking the patient. As mentioned above, such can be for defibrillation, pacing, and so on.

Processor 230 can include additional modules, such as other module 236, for other functions. In addition, if internal monitoring device 281 is indeed provided, processor 230 may receive its inputs, etc.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in functions, operations, processes, acts, actions and/or methods to be performed, and/or the processor to cause other devices or components or blocks to perform such functions, operations, processes, acts, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or be stored there after it is received by defibrillator 200.

Defibrillator 200 can optionally include a communication module 290, for establishing one or more wired or wireless communication links with other devices of other entities, such as a remote assistance center, Emergency Medical Services (EMS), and so on. The communication links can be used to transfer data and commands. The data may be patient data, event information, therapy attempted, CPR performance, system data, environmental data, and so on. For example, communication module 290 may transmit wirelessly, e.g. on a daily basis, heart rate, respiratory rate, and other vital signs data to a server accessible over the internet, for instance as described in US 20140043149. This data can be analyzed directly by the patient's physician and can also be analyzed automatically by algorithms designed to detect a developing illness and then notify medical personnel via text, email, phone, etc. Module 290 may also include such interconnected sub-components as may be deemed necessary by a person skilled in the art, for example an antenna, portions of a processor, supporting electronics, outlet for a telephone or a network cable, etc.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy-storing capacitor, and so on. Appropriate components may be included to provide for charging or replacing power source 240. In some embodiments, power source 240 is controlled and/or monitored by processor 230.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

A decision to shock can be made responsive to the shock criterion being met, as per the above-mentioned determination. When the decision is to shock, processor 230 can be configured to cause at least some or all of the electrical charge stored in module 250 to be discharged through patient 82 while the support structure is worn by patient 82, so as to deliver a shock 111 to patient 82.

For causing the discharge, defibrillator 200 moreover includes a discharge circuit 255. When the decision is to shock, processor 230 can be configured to control discharge circuit 255 to discharge through the patient at least some of all of the electrical charge stored in energy storage module 250. Discharging can be to nodes 214, 218, and from there to defibrillation electrodes 204, 208, so as to cause a shock to be delivered to the patient. Circuit 255 can include one or more switches 257. Switches 257 can be made in a number of ways, such as by an H-bridge, and so on. Circuit 255 could also be thus controlled via processor 230, and/or user interface 280.

Defibrillator 200 can optionally include other components.

Figure 3:
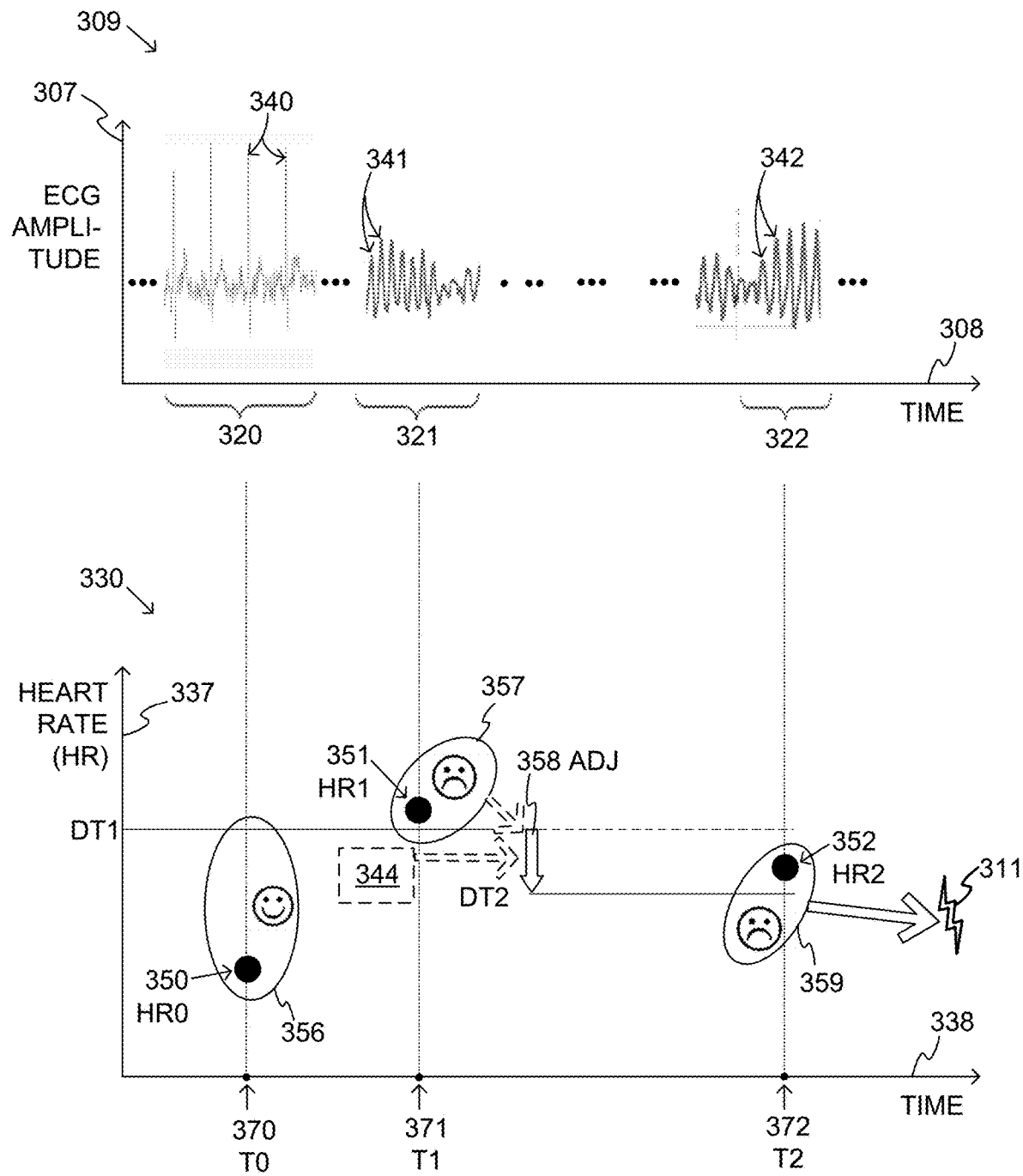
FIG. 3 shows a first time diagram of sample possible ECG signals by a patient at different time periods, and a second time diagram of heart rate values extracted from the ECG signals at the different time periods, in embodiments where a sample variable heart rate decision threshold is applied to the extracted heart rate values.

FIG. 3 shows two time diagrams 309, 330. First time diagram 309 has a horizontal TIME axis 308 and a vertical ECG AMPLITUDE axis 307. Time diagram 309 shows plots of sample possible ECG signals by an ambulatory patient at different time periods 320, 321, 322, which could be sensed by a second electrode.

Diagram 309 could be showing the sample ECG signals as they are being sensed. In embodiments, the ECG signals are sensed by sampling, which results in numerical data points that can be used for computations. These data points can be stored in memory 238. Each data point can be an ECG amplitude value together with the ordinal number ("first", "second", . . . , "thousandth", . . . ) of its sample. As such, time diagram 309 can also be obtained by plotting the contents of memory 238, understanding that the ordinal numbers represent time based on the rate of the sampling.

The following observations can be made about the sample ECG signals of diagram 309. First, all of them have peaks that are easy to identify, at least for humans viewing these diagrams. In particular, during time period 320 there are peaks 340, during time period 321 there are peaks 341, and during time period 322 there are peaks 342. Second, these peaks 340, 341, 342 are easy to identify because any noise contamination is small, and does not overwhelm these peaks. Third, the ECG signals do not look similar to each other at all the time periods, even though they are sensed from the same ambulatory patient. In fact, during time period 320 the ECG signal appears somewhat close to normal sinus rhythm, with peaks 340 that would be the R peaks of QRS complexes. In contrast, during time periods 321, 322 the ECG signal appears to indicate a heart arrhythmia, of the type that a WCD system may shock to correct.

A WCD system according to embodiments may make decisions according to specific attributes of these ECG signals. Such attributes can be extracted as numerical statistics of these ECG signals. In some embodiments, such an attribute is a heart rate (HR) of the patient. For each of these time periods 320, 321, 322, a convenient way of determining the heart rate is from peaks in the ECG signal and, more specifically, from the frequency of occurrence of such peaks. This is analogous to when a patient's heart rate is taken by sensing their pulse for beats.

As such, a WCD system according to embodiments may extract heart rate values from the sensed ECG signal, at different time periods. For this, the time periods can be judiciously chosen to provide a good measure of the frequency of occurrence of the peaks within the respective time periods. This extracting can be performed computationally by processor 230 on the acquired and stored ECG signal data values. The computations would be first for identifying the peaks, and then for determining their frequency of occurrence. This extracting may be performed in a number of ways. Such ways are shown in U.S. patent applications Ser. No. 15/948,884 and Ser. No. 16/038,007.

In FIG. 3, second time diagram 330 has a horizontal TIME axis 338 and a vertical HEART RATE (HR) axis 337. As such, axis 338 of diagram 339 corresponds with axis 308 of diagram 309, whether it is depicted as time directly, or indirectly by the ordinal numbers of the samples. Time diagram 330 shows data points HR0 350, HR1 351 and HR2 352 of extracted heart rate values at respective time points T0 370, T1 371, T2 372, which in turn correspond with time periods 320, 321, 322 of diagram 309. The heart rate values of data points HR0 350, HR1 351 and HR2 352 can also be called informally heart rates.

Time diagram 330 also shows a first decision threshold DT1, which can have units of heart rate. First decision threshold DT1 can be a threshold value of a heart rate, and is shown as an intercept on axis 337. First decision threshold DT1 can be used, alone or with criteria from other patient parameters, to determining whether or not a shock condition is met, or whether the patient should be monitored more closely to ultimately determine whether or not a shock is required, and so on. For example, the heart rate crossing first decision threshold DT1 can signify suspicion or confirmation of VT, VF, and so on.

It will be observed that heart rate value HR0 350 at time point T0 370 is less than first decision threshold DT1. A comment 356 shows a smiling-face emoticon, because this corresponds to the good case that the patient is doing well.

Later, at first time point T1 371, a first heart rate value HR1 351 is larger than first decision threshold DT1. A comment 357 shows a sad-face emoticon, because this corresponds to the bad case that the patient is experiencing a heart rate that is too high.

In embodiments, the decision threshold for the heart rate is variable. A second decision threshold DT2 is created for deciding on subsequent heart rates, which is less than first decision threshold DT1. DT2 is less than DT1 by an adjustment fraction ADJ 358. A name for this reduction of the decision threshold from DT1 to DT2 may be hysteresis. In embodiments, the adjustment fraction is at least 2%, and can be larger, for example at least 5%, 10%, etc. For instance, DT1 may be 150 beats per minute (bpm), and DT2 may be 10-20 bpm less than DT1

The reduced threshold may help with the detection of a sustaining tachycardic event such as VT/VF, and in particular with preventing the inhibiting of detection of such an event. This is because the heart rate during such an event may decrease as the condition of the heart may deteriorate. As such, second decision threshold DT2 can be created and/or maintained responsive to a number of events according to embodiments, for example responsive to having determined that first heart rate value HR1 351 is larger than first decision threshold DT1 in the first place, responsive to having determined that an optional intermediate act 344 has been performed, responsive to a critical period that has not yet passed, responsive to combinations of such events, and so on.

Second decision threshold DT2 may be used for making the same type of decision or detection for subsequently determined heart rate values. For instance, at a later second time point T2 372, a second heart rate value HR2 352 can be extracted from the ECG signals. It will be observed that second heart rate value HR2 352 is larger than second decision threshold DT2, even though second heart rate value HR2 352 is less than first decision threshold DT1. Of course, while in diagram 330 there are no heart rate values shown between time points T1 and T2, such need not be the case. In fact, multiple such hart rate values may be extracted during that time interval. In some embodiments the second lowered HR threshold DT2 advantageously helps to sustain the detection of a sustaining VT/VF event, without losing the detection when the HR drops below DT1 during such an event. For example, HR can drop below DT1 before the shock is delivered even though the same VT/VF is sustaining with a lowered HR. That risks not being detected any more, or being erroneously detected as a new event. An advantage is not losing the detection of sustaining VT/VF with HR varying around DT1.

According to a comment 359, since at time point T2 372 the patient is experiencing a heart rate that is higher than the current threshold of DT2, a certain shock 311 is administered. In other words, according to comment 359, the shock criterion is met in this example. The shock criterion could have been met from heart rate measurement HR2 352 alone, or in combination with other parameters.

While the above description was only for a single decision threshold, the invention is not so limited. In fact, in some embodiments two decision thresholds are given, namely a VT heart rate decision threshold, and also a VF heart rate threshold. In such embodiments, the VF heart rate threshold can be larger than the VT heart rate threshold. The above description can apply for making a decision in detecting either type of arrhythmia.

The devices and/or systems mentioned in this document may perform functions, processes, acts, operations, actions and/or methods. These functions, processes, acts, operations, actions and/or methods may be implemented by one or more devices that include logic circuitry. A single such device can be alternately called a computer, and so on. It may be a standalone device or computer, such as a general-purpose computer, or part of a device that has and/or can perform one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description may include flowcharts, display images, algorithms, and symbolic representations of program operations within at least one computer readable medium. An economy may be achieved in that a single set of flowcharts can be used to describe both programs, and also methods. So, while flowcharts describe methods in terms of boxes, they may also concurrently describe programs.

Methods are now described.

Figure 4:
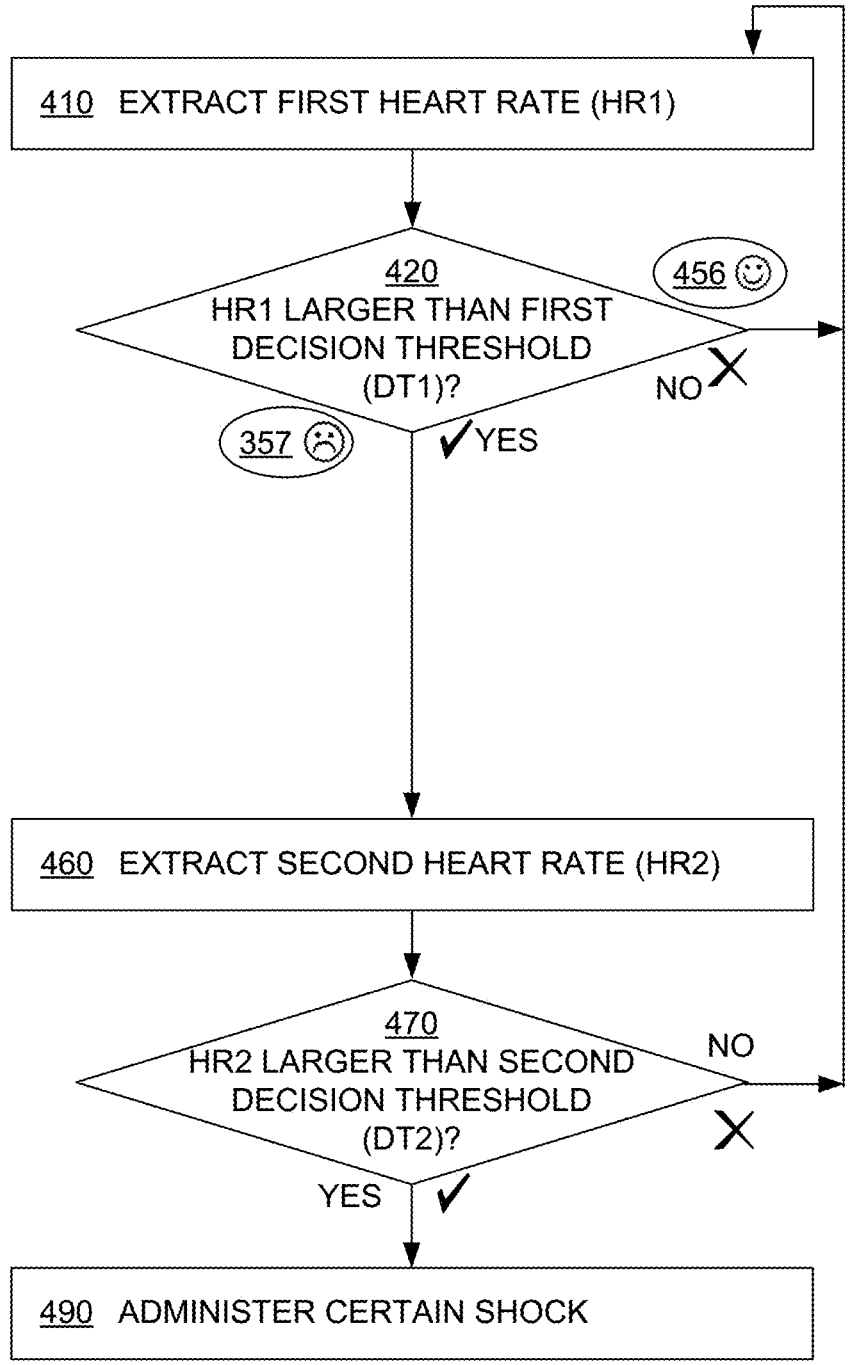
FIG. 4 is a flowchart for illustrating sample methods according to embodiments.

FIG. 4 shows a flowchart 400 for describing methods according to embodiments. According to an operation 410, a first heart rate value may be extracted from the ECG signals. An example was first heart rate value HR1 351.

According to a subsequent operation 420, it may be determined whether or not the extracted first heart rate value is larger than a first decision threshold, such as DT1. If the answer is NO, then execution may return to operation 410, and a comment 456 may apply in this case, similar to comment 356. If at operation 420 the answer is YES, then comment 357 may apply.

Moreover if, at operation 420 the answer is YES, then according to another operation 460, a second heart rate value may be extracted from the ECG signals. An example was second heart rate value HR2 352.

According to subsequent operation 470, it may be determined whether or not the second heart rate value is larger than a second decision threshold, such as DT2. As also described above, the second decision threshold is less than the first decision threshold by an adjustment fraction ADJ.

If at operation 470 the answer is NO, then execution may return to operation 410. Indeed, at such time it can be concluded that any previously detected VT/VF is not sustaining. If at operation 470 the answer is YES, meaning responsive to determining that the second heart rate value is larger than the second decision threshold, then according to another operation 490, at least some of the electrical charge stored in energy storage module 250 can be caused to be discharged via the first electrode through the ambulatory patient so as to deliver certain shock 311 to the ambulatory patient.

Figure 5:
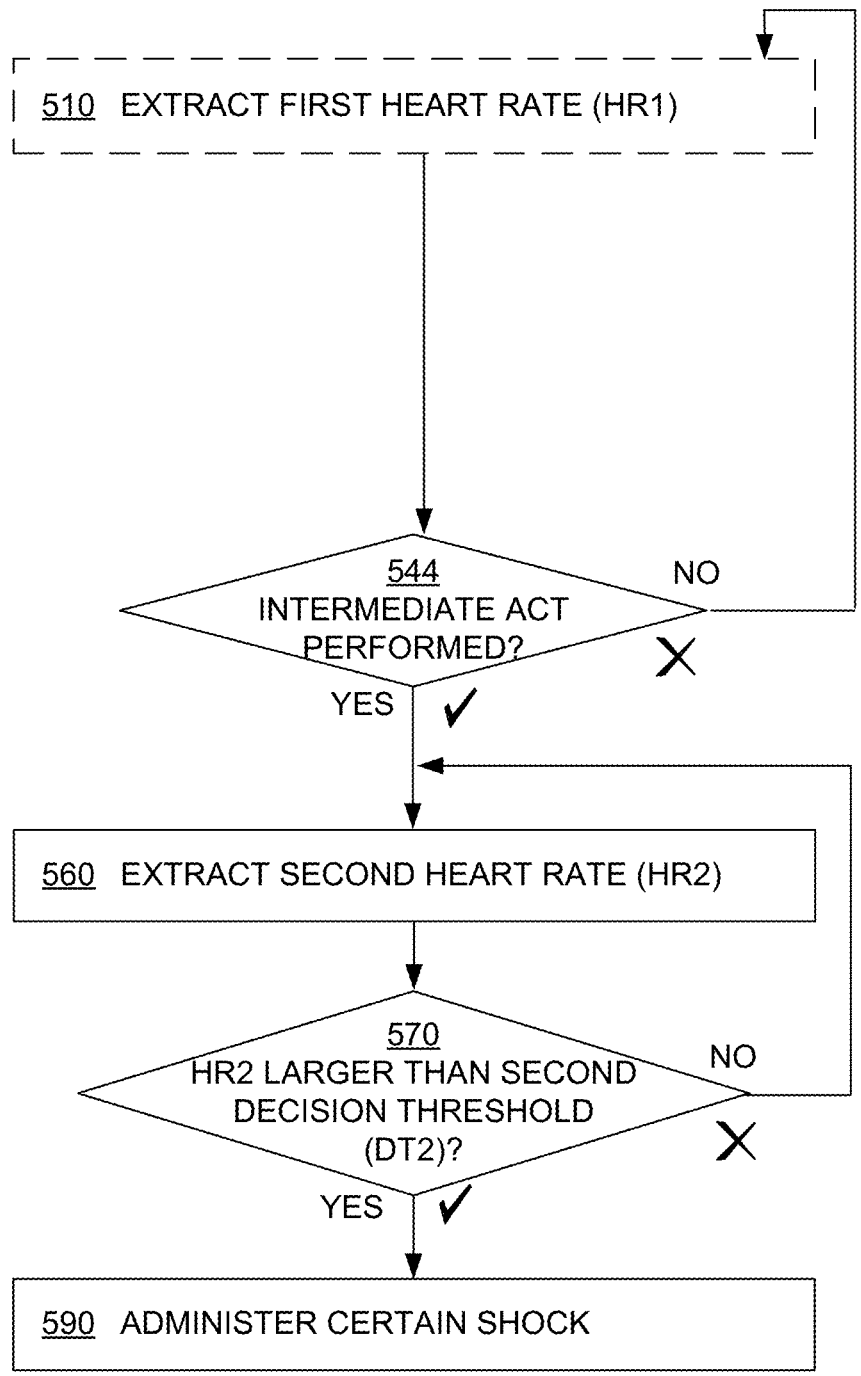
FIG. 5 is a flowchart for illustrating further sample methods according to embodiments.

FIG. 5 shows a flowchart 500 for describing methods according to embodiments. It will be appreciated that operations 510, 560, 570, 590 can be as described for operations 410, 460, 470, 490, respectively.

According to another operation 544, it may be inquired whether or not an optional intermediate act 344 has been performed. Examples of such intermediate acts are given later in this document. if the answer is NO, then execution returns to operation 510. If the answer is YES, execution proceeds to operation 560.

Examples are now described for possible intermediate act 344. In these examples, the result in flowchart 400 will be particular embodiments of operation 544.

In some embodiments, the WCD system further includes a cancel switch 289 as part of user interface 280. Cancel switch 289 can be configured to receive a shock cancel input by ambulatory patient 282. Such a shock cancel input may be received after it is determined that the first heart rate value is larger than a first decision threshold, and before the second heart rate value is extracted. In other words, a shock cancel input may be received after time point T1 371, and before time point T2 372. In such embodiments, the second decision threshold can be thus less than the first decision threshold, responsive to the shock cancel input being received. An example is are now described.

FIG. 6 shows a flowchart segment 600. Flowchart segment 600 includes an operation 644 that may be substituted in flowchart 500 of FIG. 5, in lieu of operation 544. According to operation 644, it may be determined whether or not a shock cancel input has been received. Execution from operation 644 can proceed as shown to operation 510 or 560 of flowchart 500.

Of course, in such embodiments, a patient alarm may have been rung before, for example responsive to a detection after operation 510. In such cases, the shock cancel input has likely been received responsive to the patient alarm. This may be pressed when a patient needs an extra time to prepare the therapy delivery, or a bystander can accidently push the button while panicking.

In some embodiments, processor 230 is further configured to deliver an intermediate shock to the ambulatory patient, which is distinct from certain shock 311. More particularly, processor 230 can be further configured to cause, responsive to determining that the first heart rate value is larger than the first decision threshold, at least some of the stored electrical charge to be discharged via the first electrode through the ambulatory patient so as to deliver the intermediate shock.

In such embodiments, when the second heart rate value is extracted after the intermediate shock is delivered, the second decision threshold can be thus less than the first decision threshold responsive to the intermediate shock being delivered. An example is are now described.

FIG. 7 shows a flowchart segment 700. Flowchart segment 700 includes an operation 744 that may be substituted in flowchart 500 of FIG. 5, in lieu of operation 544. According to operation 744, it may be determined whether or not an intermediate shock is delivered to the ambulatory patient. Execution from operation 744 can proceed as shown to operation 510 or 560 of flowchart 500. Of course, in such embodiments, additional heart rate values may have been extracted before and after the intermediate shock is delivered.

Returning to FIG. 4 or FIG. 5, it will be appreciated that the reduction of the decision threshold does not return to its original value. This may take place later, however. For instance, the second decision threshold may be thus less than the first decision threshold only if the second heart rate value was extracted within a critical period after the first heart rate value was extracted. In such embodiments, after that critical period passes, the heart rate decision threshold effectively returns to the original, or another related value. Examples are now described.

Figure 8:
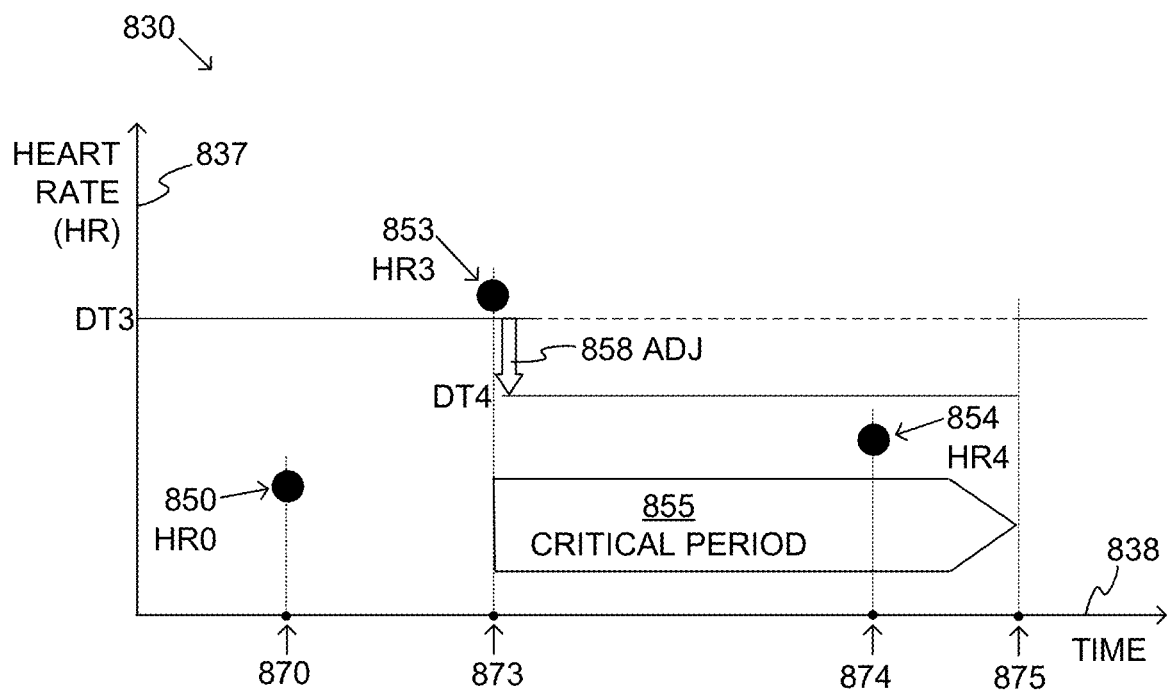
FIG. 8 is a sample time diagram similar to a time diagram of heart rate values of FIG. 3, in embodiments where a decision threshold is lowered only temporarily during a critical period.

FIG. 8 is a time diagram similar 830 to time diagram 330 of FIG. 3. Diagram 830 has a horizontal TIME axis 838 and a vertical HEART RATE (HR) axis 837. Time diagram 830 shows data points HR0 850, HR3 853 and HR4 854 of extracted heart rate values at respective time points 870, 873, 874.

Time diagram 830 also shows a first decision threshold DT3. In the example of FIG. 8, zeroth heart rate value HR0 850 is less than first decision threshold DT3, but a first heart rate value HR3 853 is larger than first decision threshold DT3. As such, the decision threshold is lowered from DT3 to become a new threshold DT4, similarly with the above. Second decision threshold DT4 is less than first decision threshold DT3 by an adjustment fraction ADJ 858.

At later second time point 874, a second heart rate value HR4 854 can be extracted from the ECG signals. It will be observed that, in this example, second heart rate value HR4 854 is less than second decision threshold DT2. As such, no decision to shock is made responsive to second heart rate value HR4 854.

A critical period 855 starts at time point 873, and lasts until a time point 875. After time point 875, the decision threshold may revert back to DT3, or to another value.

There are a number of examples of how such a critical period 855 may be defined. In some instances, more than one critical periods may be defined. A first such critical period can be 15 sec for detection. In some instances, a critical period can be set to be longer, to be really sure that the condition does not return. Or, the critical condition can be a confirmation time after the first detection at time 871, before the patient is alerted. Such confirmation times range from a fraction of a minute to maybe a few minutes. Some sample particulars are described in U.S. patent application Ser. No. 15/673,184, which was published while pending as document US 2017/0368363 A1.

In some embodiments, processor 230 is further configured to determine whether or not there is noise in the ECG signals for certain delay times. For example, large-amplitude noise can prevent peak detection in the ECG signal for these certain delay times. In such embodiments, the critical period may be increased to account for the delay time, responsive to determining that there is such noise.

Figure 9:
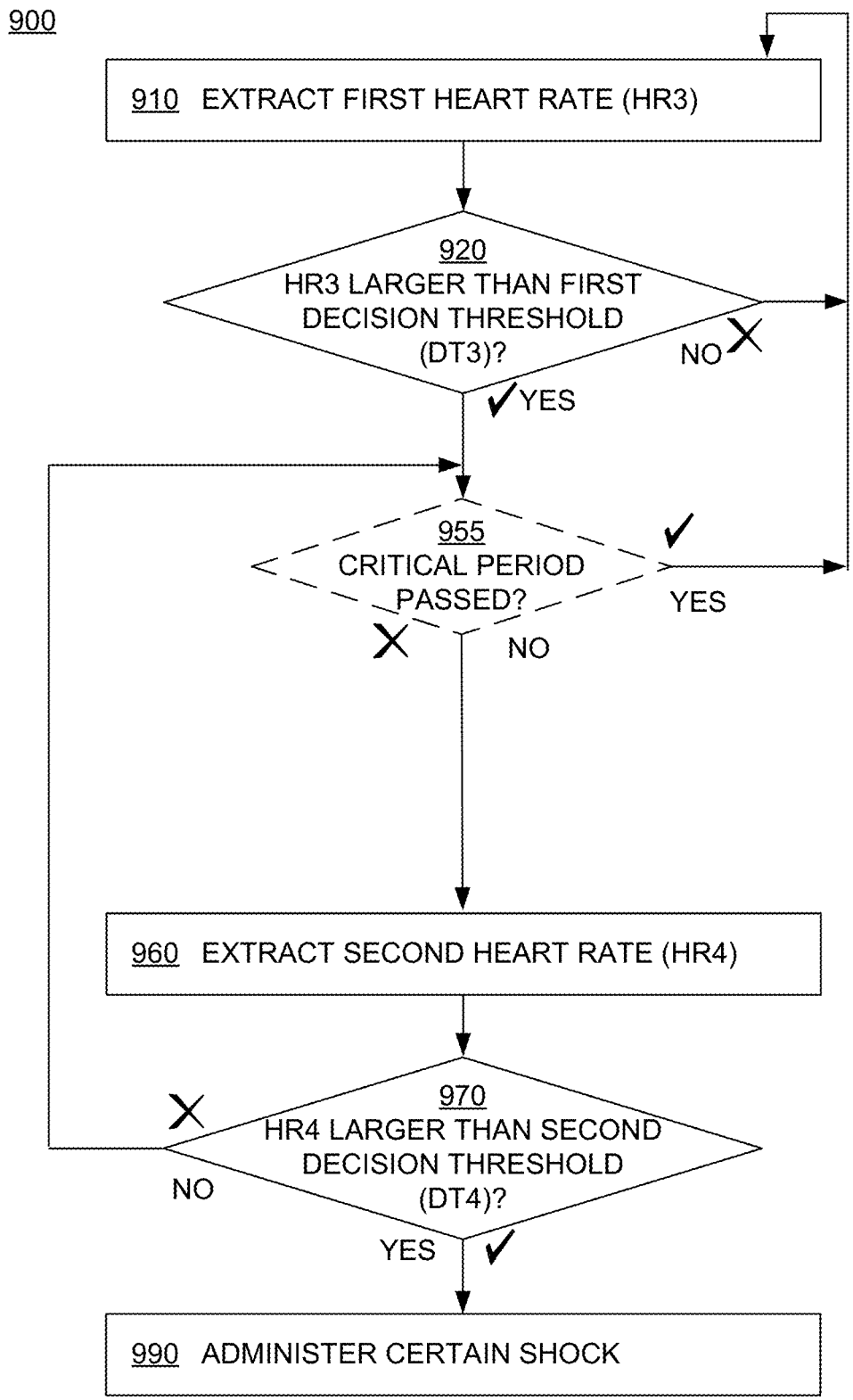
FIG. 9 is a flowchart for illustrating additional sample methods according to embodiments.

FIG. 9 shows a flowchart 900 for describing methods according to embodiments. It will be appreciated that operations 910, 920, 960, 970, 990 can be as described for operations 410, 420, 460, 470, 490, respectively.

If, at operation 920 the answer is YES, then according to another operation 955, it may be determined whether or not a critical period 855 has passed. If the answer is NO, then execution may proceed to operation 960, similarly with FIG. 4. If, however, the answer is YES, then execution may return to operation 910. This way, the decision threshold does not remain lowered to DT4 indefinitely. And, at operation 970, if the answer is NO, then execution may return to operation 910 or 955.

Figure 10:
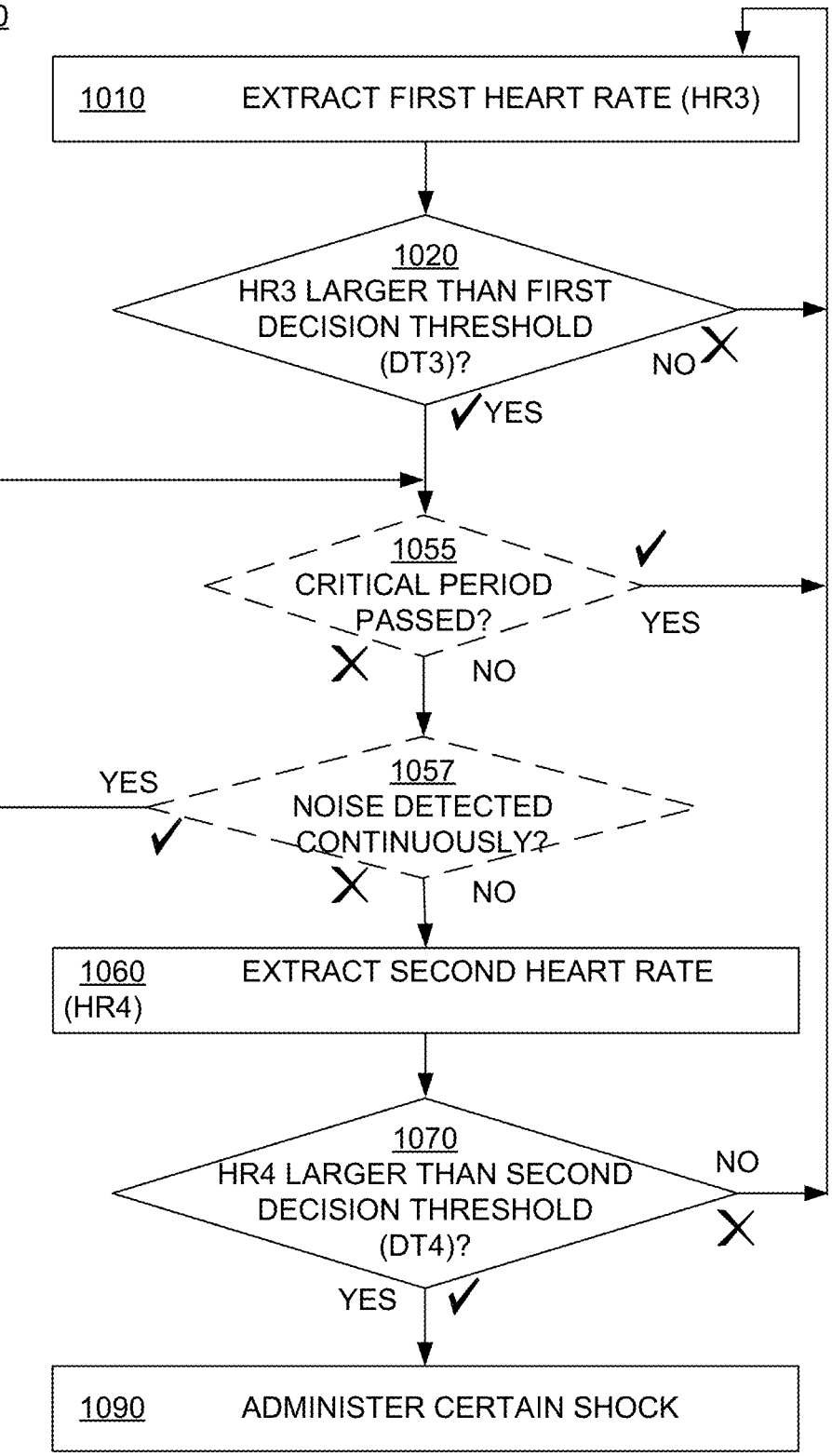
FIG. 10 is a flowchart for illustrating further sample methods according to embodiments.

FIG. 10 shows a flowchart 1000 for describing methods according to embodiments. It will be appreciated that operations 1010, 1020, 1055, 1060, 1070, 1090 can be as described for operations 910, 920, 955, 960, 970, 990, respectively, but with different routing of decisions.

According to another operation 1057, it is determined whether or not noise is detected continuously. lithe answer is NO, then execution may proceed to operation 1060. If the answer is YES, then execution may return to operation 1055, and the critical period may be that of noise.

In the methods described above, each operation can be performed as an affirmative act or operation of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description.

Some technologies or techniques described in this document may be known. Even then, however, it does not necessarily follow that it is known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

In this description a single reference numeral may be used consistently to denote a single item, aspect, component, or process. Moreover, a further effort may have been made in the drafting of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that the claim can have one or more of this component or this item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A wearable cardioverter defibrillator (WCD) system for an ambulatory patient, comprising:
   an energy storage module configured to store an electrical charge;
   a first electrode;
   a second electrode configured to sense an electrocardiogram (ECG) signals of the ambulatory patient;
   a support structure configured to be worn by an ambulatory patient so as to maintain the first electrode and the second electrode on a body of the ambulatory patient; and
   a processor configured to:
   extract a first heart rate value from the ECG signals sensed by the second electrode,
   then determine whether or not the first heart rate value is larger than a first decision threshold,
   then extract a second heart rate value from the ECG signals,
   determine whether or not the second heart rate value is larger than a second decision threshold, the second decision threshold being less than the first decision threshold by an adjustment fraction, the adjustment fraction being at least 2%, and
   cause, responsive to determining that the second heart rate value is larger than the second decision threshold, at least some of the stored electrical charge to be discharged via the first electrode through the ambulatory patient so as to deliver a certain shock to the ambulatory patient.

2. The WCD system of claim 1, in which
   the adjustment fraction is at least 5%.

3. The WCD system of claim 1, in which
   the second decision threshold is less than the first decision threshold by the adjustment fraction responsive to having determined that the first heart rate value is larger than the first decision threshold.

4. The WCD system of claim 1, further comprising:
   a cancel switch configured to receive a shock cancel input, and in which
   a shock cancel input is received after it is determined that the first heart rate value is larger than a first decision threshold and before the second heart rate value is extracted, and
   the second decision threshold is thus less than the first decision threshold responsive to the shock cancel input having been received.

5. The WCD system of claim 1, in which
   the processor is further configured to cause, responsive to determining that the first heart rate value is larger than the first decision threshold, at least some of the stored electrical charge to be discharged via the first electrode through the ambulatory patient so as to deliver an intermediate shock to the ambulatory patient before the second heart rate value is extracted, the intermediate shock distinct from the certain shock, and
   the second decision threshold is thus less than the first decision threshold responsive to the intermediate shock being delivered.

6. The WCD system of claim 1, in which
   the second decision threshold is thus less than the first decision threshold responsive to the second heart rate value being extracted within a critical period after the first heart rate value was extracted.

7. The WCD system of claim 6, in which
   the processor is further configured to:
   determine whether or not there is noise in the ECG signals for a certain delay time, and
   the critical period is increased to account for the delay time responsive to determining that there is noise in the ECG signals.

8. A non-transitory computer-readable storage medium storing one or more programs which, when executed by at least one processor of a wearable cardioverter defibrillator (WCD) system, the WCD system including an energy storage module storing an electrical charge, a first electrode, a second electrode sensing an electrocardiogram (ECG) signals of the ambulatory patient, a support structure configured to be worn by an ambulatory patient so as to maintain the first electrode and the second electrode on a body of the ambulatory patient, these one or more programs result in operations comprising:
   extracting a first heart rate value from the ECG signals sensed by the second electrode;
   then determining whether or not the first heart rate value is larger than a first decision threshold;
   then extracting a second heart rate value from the ECG signals;
   determining whether or not the second heart rate value is larger than a second decision threshold, the second decision threshold being less than the first decision threshold by an adjustment fraction, the adjustment fraction being at least 2%; and
   causing, responsive to determining that the second heart rate value is larger than the second decision threshold, at least some of the stored electrical charge to be discharged via the first electrode through the ambulatory patient so as to deliver a certain shock to the ambulatory patient.

9. The medium of claim 8, in which
   the adjustment fraction is at least 5%.

10. The medium of claim 8, in which
    the second decision threshold is less than the first decision threshold by the adjustment fraction responsive to having determined that the first heart rate value is larger than the first decision threshold.

11. The medium of claim 8, in which
    the WCD system further includes a cancel switch, and
    when the one or more programs are executed by the at least one processor, the operations further comprise:
    receiving, by the cancel switch a shock cancel input after it is determined that the first heart rate value is larger than a first decision threshold and before the second heart rate value is extracted, and
    in which the second decision threshold is thus less than the first decision threshold responsive to the shock cancel input having been received.

12. The medium of claim 8, in which when the one or more programs are executed by the at least one processor, the operations further comprise:
    cause, responsive to determining that the first heart rate value is larger than the first decision threshold, at least some of the stored electrical charge to be discharged via the first electrode through the ambulatory patient so as to deliver an intermediate shock to the ambulatory patient before the second heart rate value is extracted, the intermediate shock distinct from the certain shock, and
    in which the second decision threshold is thus less than the first decision threshold responsive to the intermediate shock being delivered.

13. The medium of claim 8, in which
the second decision threshold is thus less than the first decision threshold responsive to the second heart rate value being extracted within a critical period after the first heart rate value was extracted.

14. The medium of claim 13, in which
it is further determined whether or not there is noise in the ECG signals for a certain delay time, and
the critical period is increased to account for the delay time responsive to determining that there is noise in the ECG signals.

15. A method for a wearable cardioverter defibrillator (WCD) system, the WCD system including an energy storage module storing an electrical charge, a first electrode, a second electrode sensing an electrocardiogram (ECG) signals of the ambulatory patient, a support structure configured to be worn by an ambulatory patient so as to maintain the first electrode and the second electrode on a body of the ambulatory patient, and a processor, the method comprising:
extracting a first heart rate value from the ECG signals sensed by the second electrode;
then determining whether or not the first heart rate value is larger than a first decision threshold;
then extracting a second heart rate value from the ECG signals;
determining whether or not the second heart rate value is larger than a second decision threshold, the second decision threshold being less than the first decision threshold by an adjustment fraction, the adjustment fraction being at least 2%; and
causing, responsive to determining that the second heart rate value is larger than the second decision threshold, at least some of the stored electrical charge to be discharged via the first electrode through the ambulatory patient so as to deliver a certain shock to the ambulatory patient.

16. The method of claim 15, in which
the adjustment fraction is at least 5%.

17. The method of claim 15, in which
the second decision threshold is less than the first decision threshold by the adjustment fraction responsive to having determined that the first heart rate value is larger than the first decision threshold.

18. The method of claim 15, in which
the WCD system further includes a cancel switch, and
further comprising: receiving, by the cancel switch a shock cancel input after it is determined that the first heart rate value is larger than a first decision threshold and before the second heart rate value is extracted, and
in which the second decision threshold is thus less than the first decision threshold responsive to the shock cancel input having been received.

19. The method of claim 15, further comprising:
cause, responsive to determining that the first heart rate value is larger than the first decision threshold, at least some of the stored electrical charge to be discharged via the first electrode through the ambulatory patient so as to deliver an intermediate shock to the ambulatory patient before the second heart rate value is extracted, the intermediate shock distinct from the certain shock, and
in which the second decision threshold is thus less than the first decision threshold responsive to the intermediate shock being delivered.

20. The method of claim 15, in which
the second decision threshold is thus less than the first decision threshold responsive to the second heart rate value being extracted within a critical period after the first heart rate value was extracted.

21. The method of claim 20, in which
it is further determined whether or not there is noise in the ECG signals for a certain delay time, and
the critical period is increased to account for the delay time responsive to determining that there is noise in the ECG signals.

\* \* \* \* \*